US006451329B1

(12) United States Patent
Sandewicz et al.

(10) Patent No.: US 6,451,329 B1
(45) Date of Patent: Sep. 17, 2002

(54) COSMETIC COMPOSITIONS FOR REDUCING SHINY APPEARANCE OF OILY SKIN

(75) Inventors: Ida Marie Sandewicz, Monroe Township; Tatyana Zamyatin, Princeton Junction; Julio Gans Russ, Westfield, all of NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/810,134

(22) Filed: Mar. 16, 2001

(51) Int. Cl.7 ................................................ A61K 9/00
(52) U.S. Cl. .................. 424/401; 424/274.1; 424/688; 424/63; 424/64; 424/69; 424/70.12; 424/70.28; 514/937; 514/938; 514/844; 514/845; 514/846; 516/22; 516/53
(58) Field of Search ............................... 424/401, 274.1, 424/63, 64, 69, 70.12, 70.28, 688; 514/937, 938, 844, 845, 846; 516/22, 53

(56) References Cited

U.S. PATENT DOCUMENTS 5,800,816 A * 9/1998 Brieva et al. .................. 424/63

FOREIGN PATENT DOCUMENTS

| JP | 11263732 | * | 9/1999 |
| JP | 2977582 | * | 11/1999 |

* cited by examiner

Primary Examiner—Thurman K. Page
Assistant Examiner—Lakshmi Channavajjala
(74) Attorney, Agent, or Firm—Julie Blackburn

(57) ABSTRACT

A pigmented emulsion cosmetic composition for reducing the shiny appearance of skin and cosmetically improving the appearance of skin imperfections comprising a cosmetically effective amount of mushroom extract and a method for reducing the shiny appearance of skin and cosmetically improving the appearance of skin imperfections comprising applying to the skin an emulsion cosmetic composition containing mushroom extract.

18 Claims, No Drawings

COSMETIC COMPOSITIONS FOR REDUCING SHINY APPEARANCE OF OILY SKIN

TECHNICAL FIELD

The invention is in the field of cosmetic composition for application to skin.

BACKGROUND OF THE INVENTION

Oil and sebaceous secretions protect facial skin against moisture loss by forming a superficial film on the skin surface that locks in skin moisture. In general, reduced oil secretion causes dry skin and excessive oil secretion causes oily skin. Ideally the skin should be balanced, which means that the skin should secrete exactly the correct amount of oil to keep the skin hydrated and smooth, but not enough oil to give the undesirable shiny appearance or promote blemish formation. Since facial skin is rarely perfect, cosmetic manufacturers must formulate their products to ameliorate less than perfect skin types.

One particularly undesirable feature of oily skin is the resulting shine that quickly appears on the skin surface as oil is secreted by the skin. Shiny skin looks greasy. It also tends to show more imperfections than skin that exhibits a matte surface. One standard method of treating shiny, oily skin, is to apply cosmetics that contain various types of particulate absorbent agents. One example of such a product is "Cornsilk" a commercial loose powder. When the powder is applied to oily skin the various types of particulates absorb excess skin oil and matte the skin. One problem with Cornsilk and other products containing oil-absorbing particulates is that the particulates cake or streak in addition to providing a mask-like effect when the application is too heavy. In addition, layers of oil-laden particulates on the skin can clog skin pores and promote blemish formation.

Another approach to counteracting oily skin is found in the so-called "oil-free" cosmetic formula. The idea behind these products is not to aggravate the oily condition by adding oils to the cosmetic the user will apply to skin that already secretes too much oil. Low viscosity silicone oils, which tend to flash off fairly soon after the cosmetic is applied to the skin, are typically used in these formulas. One problem with "oil-free" formulas is that they do nothing to ameliorate the effects of excessive oil. Nor do such formulas do anything to minimize the undesirable shiny appearance of oily skin.

Clearly there is a need for cosmetic formulas that are capable of reducing the undesirable shiny appearance of skin having excessive oil on its surface, without overly matting the skin with absorbents that give a cakey, made-up look.

Most unexpectedly, it has been discovered that cosmetics formulated with mushroom extract are excellent for use on all skin types including oily skins. Such cosmetics are able to reduce the shiny appearance of skin and thereby aid in cosmetically improving the appearance of skin imperfections such as blemishes, wrinkles, and fine lines. At the same time these formulas do not provide the heavy made-up look that is often seen in compositions containing oil-blotting absorbent powders.

It is an object of the invention to provide a cosmetic formula for reducing the shiny appearance of skin having excess oil on its surface.

It is further object of the invention to provide a cosmetic formula for cosmetically improving the appearance of skin imperfections such as fine lines, wrinkles, and blemishes.

It is a further object of the invention to provide a pigmented emulsion foundation makeup for ameliorating the adverse effects of oily skin.

SUMMARY OF THE INVENTION

The invention comprises a pigmented emulsion cosmetic composition for reducing the shiny appearance of skin and cosmetically improving the appearance of skin imperfections, comprising a cosmetically effective amount of mushroom extract.

A method for reducing the shiny appearance of skin and cosmetically improving the appearance of skin imperfections, comprising applying to the skin a pigmented emulsion cosmetic composition comprising a cosmetically effective amount of mushroom extract.

The cosmetic composition and method of the invention is suitable for use on dry, normal, oily, or combination skin types. The resulting composition and method reduces the shiny appearance of oily skin and cosmetically improves the appearance of skin imperfections such as wrinkles, fine lines, and blemishes. The applied cosmetic provides a smooth, natural finish on skin.

DETAILED DESCRIPTION

All percentages mentioned herein are percentages by weight unless otherwise indicated.

I. The Composition

The composition of the invention comprises a pigmented emulsion cosmetic composition for reducing the shiny appearance of skin and cosmetically improving the appearance of skin imperfections, comprising a cosmetically effective amount of mushroom extract.

The term "reducing the shiny appearance of skin" means that the cosmetic composition containing an effective amount of mushroom extract, when applied to skin, reduces the shiny appearance of skin.

The emulsion composition may be a water-in-oil or oil-in-water emulsion comprising about 0.1–95%, preferably about 0.5–85%, more preferably about 1–75% water and about 0.5–35%, preferably about 1–25%, more preferably about 1.5–20% oil. Preferably the emulsion composition is an oil-in-water emulsion. The ingredients that may be found in this composition are further described below.

A. Mushroom Extract

The claimed composition comprises a cosmetically effective amount of mushroom extract. Generally, a cosmetically effective amount ranges from about 0.01–10%, preferably about 0.05–8%, more preferably about 0.1–7%. These percentages refer to the mushroom content only, not any liquid in which it is dispersed. The mushroom extract is preferably extracted from the pulp of a mushroom of the genus Fomes or Polyporus, e.g. *Fomes officinalis* or *Polyporus officinalis*. Particularly preferred is a mushroom extract sold under the tradename Laricyl® by Laboratoires Serobiologique. Laricyl® is an amber liquid having a pH ranging from 4.8 to 5.2 and a refractive index of 1.388 to 1.396 and is comprised of a solution of butylene glycol and mushroom extract having the INCI name Butylene Glycol (and) Mushroom (*Fomes officinalis*) extract.

Preferably the mushroom extract comprises mushroom pulp contact that is soluble at room temperature in butylene glycol—for example, sufficiently soluble as to be capable of forming a solution concentration of at least about 5% at room temperature.

B. Oil

The emulsion cosmetic composition comprises one or more types of oils that may be volatile, non-volatile or mixtures thereof. Preferably the total oil content is in the range of about 0.5–75%, preferably 1–70%, more preferably 5–65% by weight of the total composition. The term "volatile" means that the oil has a vapor pressure of at least 2 mm. of mercury at 20° C. The term "non-volatile" means that the oil has a vapor pressure of less than 2 mm. of mercury at 20° C. Either silicone or organic oils are suitable provided that the oils are compatible, i.e. soluble in each other.

1. Volatile Oils

Suitable volatile oils include silicones cyclic silicones having the general formula:

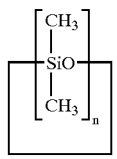

where n=3–6.

Also suitable are linear volatile silicones in accordance with the invention have the general formula:

where n=0–6.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisitoxane, and mixtures thereof Also suitable as the volatile oils are various straight or branched chain paraffinic hydrocarbons having about 5 to 40 carbon atoms, more preferably about 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818, 105, both of which are hereby incorporated by reference. Preferred volatile paraffinic hydrocarbons have a molecular weight of about 70–225, preferably about 160 to 190 and a boiling point range of about 30 to 320, preferably 60–260 degrees C., and a viscosity of less than about 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable.

The preferred composition comprises about 1–45%, preferably about 2–40%, more preferably about 3–35% by weight of the total composition of volatile oil. Preferred is where the volatile oil is a linear or cyclic silicone.

2. Non-Volatile Oils

The claimed composition may contain one or more non-volatile oils such as silicone or organic oils. Preferably, the composition contains silicone oils either alone or in combination with small amounts of organic oil.

A. Silicones

Suitable nonvolatile silicones include water insoluble silicones having a viscosity of about 10 to 600,000 centistokes, preferably about 20 to 100,000 centistokes at 25° C. Suitable water insoluble silicones include cetyl dimethicone, dimethicone, phenyl trimethicone, phenyldimethicone, diphenyl dimethicone, and mixtures thereof. Such silicones are available from Dow Corning as the 3225C formulation aid, Dow 190 and 193 fluids, or similar products marketed by Goldschmidt under the ABIL tradename.

Also suitable as the nonvolatile silicone oil are various fluorinated silicones such as trimethylsilyl endcapped fluorosilicone oil, polytrifluoropropylmethylsiloxanes, and similar silicones such as those disclosed in U.S. Pat. No. 5,118, 496 which is hereby incorporated by reference.

Preferably, the makeup compositions comprise a mixture of volatile and non-volatile silicones, in particular, about 3–35% by weight of the total composition of volatile silicone oil, and about 0.1–25%, preferably about 0.5–20%, more preferably about about 1–15% nonvolatile silicone. The presence of the volatile silicone enables the makeup to dry on the skin in an appropriate period of time, and minimizes the heavy, greasy feel that is occasionally found with nonvolatile oils. The remaining nonvolatile oil phase acts to plasticize the film formed on the skin by the dried cosmetic composition.

B. Organic Oils

The claimed composition may comprise one or more organic oils, and if so, they are preferably low viscosity organic oils. Suggested ranges of organic oils are about 0.01–20%, preferably about 0.05–15%, more preferably about 0.1–10%. Preferred viscosity ranges for the organic oil are 10–1000, preferably 15–800, more preferably about 20–800 centipoise at 25° C.

Suitable organic oils include esters, (e.g. glyceryl esters), paraffinic hydrocarbons, and the like as disclosed in U.S. Pat. No. 5,800,816, which is hereby incorporated by reference.

C. Pigments

The composition of this invention is a pigmented emulsion cosmetic composition. The term "pigment" when used in accordance with the invention means the composition contains one or more inorganic or organic particulates or colorants that are water soluble or water insoluble. A pigment in accordance with the invention may provide color, whiteness, opacity, sunscreen activity, or be capable of muting color. For example, particulates that are generally deemed to provide white color, opacity, sunscreen protection, or color muting effects to a cosmetic composition are considered "pigments" in accordance with the claimed invention. Examples of such ingredients include inorganic metal oxides such as titanium dioxide, zinc oxide; as well as bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, rice starch, silica, talc, mica, titanium dioxide, alumina, calcium carbonate, calcium silicate, dextran, nylon, silica silylate, silk powder, sericite, soy flour, tin oxide, titanium hydroxide, trimagnesium phosphate, walnut shell powder, and so on.

Suitable ingredients that provide blue, red, green, and yellow color to a cosmetic composition are inorganic metal oxides, in particular iron oxides such as black, red, green, yellow, and so on.

Also suitable are organic pigments including various aromatic types such as azo, indigoid, triphenylmethane, anthraquinone, and xanthine dyes which are designated as D&C and FD&C blues, browns, greens, oranges, reds, yellows, etc. Organic pigments also generally consist of insoluble metallic salts of certified color additives, referred to as the Lakes.

If desired, the pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Particularly preferred are silicone treated pigments as disclosed in U.S. Pat. No. 5,143,722, which is hereby incorporated by reference.

Preferably, the particle size of the particulates ranges from about 0.05 to 150 microns, and are present in ranges of about 0.1–20%, preferably about 0.5–15%, more preferably about 1–10% by weight of the total composition.

It is particularly preferred that the compositions of the invention comprise very fine particle zinc oxide and/or titanium dioxide, in addition to the other pigments and particulates which may be present. The mixture of zinc oxide and titanium dioxide causes the composition to exhibit a sun protective factor (SPF), possibly as high as 10 to 20 SPF. Preferred particle sizes of the zinc oxide and titanium dioxide are about 0.005 to 10 microns. Preferably the compositions of the invention contain about 1–15% by weight of the composition of zinc oxide, titanium dioxide, or mixtures thereof, having a particle size of about 0.005 to 10 microns and providing makeup having an SPF of 10 to 20, preferably about 15 to 20.

In the preferred embodiment of the invention a portion of the pigments are spherical in shape. In particular, about 0.01–5% of the pigments used are preferably spherical, preferably having a cross sectional diameter of about 10 to 80 microns. Examples of such pigments include boron nitride, nylon, spherical silica, and the like. The spherical cross section of the pigments provides a very smooth feel and blendability to the composition. Blendability means that when the composition is applied to skin it blends very easily into the skin surface with the spherical pigments exhibiting a roller ball effect. The spherical particle size also causes the film to feel very smooth on the skin surface.

D. Surfactants

The claimed emulsion compositions may exist in two separate phases that are emulsified upon shaking. Preferably the claimed compositions contain an effective amount of one or more surfactants that cause the dispersed phase to remain emulsified in the continuous phase to form an emulsion having stability which is suitable for commercial purposes. Suggested ranges of surfactants are about 0.01–20%, preferably about 0.1–15%, more preferably about 0.5–10%. Suitable surfactants include silicone surfactants or organic surfactants, which may be anionic, cationic, nonionic, zwitterionic, or amphoteric. Preferably the surfactants are nonionic organic or silicone surfactants.

1. Silicone Surfactants

Preferred are nonionic silicone surfactants having at least one hydrophilic radical and at least one lipophilic radical. These silicone surfactants may be a liquid or solid at room temperature and are water-in-oil or oil-in-water type surfactants which have an Hydrophile/Lipophile Balance (HLB) of about 2 to 18. Preferably the silicone surfactant is a nonionic surfactant having an HLB of about 2 to 12, preferably about 2 to 10, most preferably about 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

The polymeric silicone surfactant used in the invention may have any of the following general formulas:

$$M_xQ_y, \text{ or}$$

$$M_xT_y, \text{ or}$$

$$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof T is a trifunctional siloxy unit having the empirical formula R'SiO$_{1.5}$ or RSiO$_{1.5}$ wherein R is methyl and R' is a C$_{2-22}$ alkyl or phenyl. Q is a quadrifunctional siloxy unit having the empirical formula SiO$_{4/2}$, and D, D', D", x, y, and z are as set forth below, with the proviso that the compound contains at least one hydrophilic radical and at least one lipophilic radical. Preferred is a linear silicone of the formula:

$$MD_xD'_yD''_zM$$

wherein M=RRRSiO$_{1/2}$

D and D'=RR'SiO$_{2/2}$

D"=RRSiO$_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy

D=Si[(CH$_3$)][(CH$_2$)$_n$CH$_3$]O$_{2/2}$ where n=0–40,

D'=Si [(CH$_3$)][(CH$_2$)$_o$—O—PE)]O$_{2/2}$ where PE is (—C$_2$H$_4$O)$_a$(—C$_3$H$_6$O)$_b$H, o=0–40, a=1–100 and b=1–100, and D"=Si (CH$_3$)$_2$O$_{2/2}$ More specifically, suitable silicone surfactants have the formula:

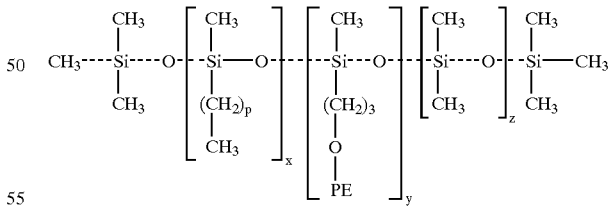

wherein p is 0–40, and

PE is (—C$_2$H$_4$O)$_a$(—C$_3$H$_6$O)$_b$—H where x, y, z, a, and b are such that the maximum molecular weight of the polymer is approximately 50,000.

Another type of preferred organosiloxane emulsifier suitable for use in the compositions of the invention are emulsifiers sold by Union Carbide under the Silwet™ trademark, which are referred to by the CTFA term "dimethicone copolyol".

Also suitable as nonionic silicone surfactants are hydroxy-substituted silicones such as dimethiconol, which is defined as a dimethyl silicone substituted with terminal hydroxy groups.

Examples of suitable silicone surfactants are those sold by Dow Corning under the tradename Dow Corning 3225C Formulation Aid, Dow Corning 190 Surfactant, Dow Corning 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

2. Organic Surfactants

Also suitable for use are one or more organic surfactants, preferably nonionic organic surfactants. Examples of nonionic organic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Beheneth 5-30, which is formed by the reaction of behenyl alcohol and ethylene oxide where the number of repeated ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, laureth, 1-100 where the number of repeating ethylene oxide units is 1 to 100, and so on. Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol.

Also suitable as the nonionic surfactant are alkyoxylated carboxylic acids, which are formed by the reaction of a carboxylic acid with an alkylene oxide or with a polymeric ether. The resulting products have the general formula:

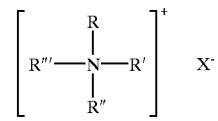

or

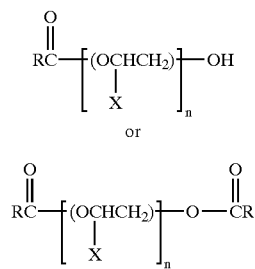

where RCO is the carboxylic ester radical, X is hydrogen or lower alkyl, and n is the number of polymerized alkoxy groups. In the case of the diesters, the two RCO- groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

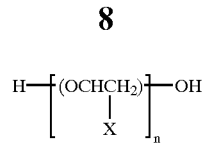

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20-85, sorbitan oleate, sorbitan palmitate, sorbitan sesquiisostearate, sorbitan stearate, and so on.

In the preferred compositions of the invention, the nonionic surfactant is selected from an nonionic organic surfactant, in particular a nonionic silicone surfactant, more specifically dimethicone copolyol.

E. Skin Conditioning Agents

Preferably, the compositions comprise one or more skin conditioning agents in ranges from about 0.01–20%, preferably about 0.1–15%, more preferably about 0.5–10% by weight of the total composition. The skin conditioning agents are capable of moisturizing skin without promoting oil secretion or contributing to oil on the skin surface. In particular, it is well known that oily skin can still be dry due to inadequate moisture in the skin tissue. The skin conditioning agents used herein address the moisture and hydration needs of skin and have no negative impact on skin oils. Suitable skin conditioning agents include a variety of organic compounds and polymers.

1. Quaternary Ammonium Compounds

Particularly suitable for use as skin conditioning agents are quaternary ammonium compounds. These ingredients may be monomeric or polymeric and are positively charged tetra-substituted nitrogen derivatives having the following general structure:

$$\left[ \begin{array}{c} R \\ | \\ R'''\!\!-\!\!N\!\!-\!\!R' \\ | \\ R'' \end{array} \right]^+ \quad X^-$$

wherein R, R', R" and R'" may be the same or different but may not be hydrogen, and R, R', R", and R'" are selected from $C_{1-30}$ straight or branched alkyl, and wherein X' represents an anion such as chloride, ammonium, methosulfate, and the like.

Preferred are quaternary ammonium polymers referred to as Polyquaternium having a numerical designation from 1 to 51. Examples of such polymers are Polyquaternium-4 which is a copolymer of hydroxyethylcellulose and diallyldimethyl ammonium chloride, Polyquaternium-5 which is a copolymer of acrylamide and bet- methacrylyloxyethyl trimethyl ammonium methosulfate, Polyquaternium-6 which is a copolymer of dimethyl diallylammonium chloride, Polyquaternium-7 which is a polymeric quaternary ammonium salt consisting of acrylamide and dimethyldiallyl ammonium chloride, Polyquaternium-8 which is a polymeric quaternary ammonium salt of methyl and stearyl dimethylaminoethyl methacrylate quaternized with dimethyl sulfate, and so on. Particularly preferred is Polyquaternium-51 which is a copolymer of butyl-2-methyl-2-propenoate and an ester of orthphosphoric acid. Polyquaternium-51 has the chemical name 3,5,8-triox-4- phosphaundec-10-en-1-aminium, 4-hydroxy-N,N,N,1-tetramethyl-9-oxo, inner salt 4-oxide polymer with butyl-2-methyl-2-propenoate. Polyquatemium 51 is available from Collaborative Laboratories under the tradename Lipidure.

2. Alcohols

Various aliphatic or aromatic mono-, di- or polyfunctional organic alcohols may be used as skin conditioning agents in the composition of the invention. Generally, such alcohols have the formula R—OH wherein R is a straight or branched $C_{2-30}$ alkyl or $C_{2-30}$ alkyl amido alkyl, or $C_{2-30}$ alkyl amido alkoxy. Preferably R has one or more substituted hydroxyl groups, making R—OH polyhydric. The alcohol may also be the dispersant, e.g. the extracting liquid, for the mushroom extract. Examples of such alcohols include butylene glycol, ethylene glycol, glycerin, propylene glycol, panthenol, panthenyl ethyl ether, and phytantriol. Panthenol is a trihydric alcohol of the formula R—OH wherein R is an alkyl amido alkyl having two substituted hydroxyl groups. It has the formula:

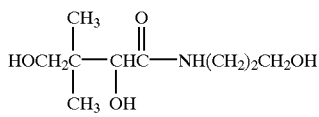

Panthenyl ethyl ether, a monohydric alcohol, is the ethyl ether of panthenol having the formula:

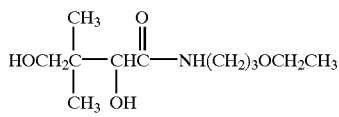

Phytantriol is an aliphatic polyhydric alcohol having the general formula:

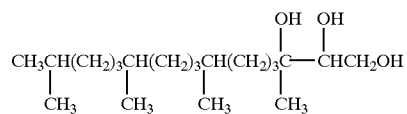

Particularly preferred are composition comprising one or more skin conditioning agents selected from a quaternary ammonium compound and an alcohol. Such compositions preferably comprise about 0.01–5% of the quaternary ammonium compound and about 0.01–10% of one or more alcohols.

F. Film Forming Ingredients

The preferred compositions in accordance with the invention comprise one or more film formers that, upon drying, will aid in forming a continuous cosmetic film on the skin. The film former may be present in an amount of about 0.1–45%, preferably about 0.5–20%, more preferably about 1–15% by weight of the total composition. The film formers may advantageously be resinous plant extracts or synthetic polymers.

1. Resinous Plant Extracts

Examples of resinous plant extracts that provide film forming properties include materials such as rosin and shellac, or derivative thereof.

2. Synthetic Polymeric Film Formers

Suitable synthetic polymers may be silicone or organic based. Particularly preferred are siloxy silicate polymers having the following general formula:

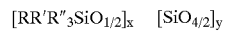

wherein R, R' and R" are each independently a $C_{1-10}$ straight or branched chain alkyl or phenyl, and x and y are such that the ratio of $(RR'R")_3SiO_{1/2}$ units to $SiO_2$ units is 0.5 to 1 to 1.5 to 1.

Preferably R, R' and R" are each a $C_{1-6}$ alkyl, and more preferably are methyl and x and y are such that the ratio of $(CH_3)_3SiO_{1/2}$ units to $SiO_{4/2}$ units is about 0.75 to 1. Most preferred is this trimethylsiloxy silicate containing 2.4 to 2.9 weight percent hydroxyl groups, which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40–60% volatile silicone and 40–60% trimethylsiloxy silicate. Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

Also suitable are synthetic polymers that are often found in the form of an aqueous dispersion where the polymer particles are dispersed in the aqueous phase of the polymer emulsion. Examples of such polymers include homo- or copolymers of monomers such as acrylic acid, methacrylic acid or $C_{1-30}$ esters of acrylic or methacrylic acid, vinyl pyrrolidone, vinyl acetate, urethane, $C_{1-30}$ hydroxy esters of acrylic or methacrylic acid, vinyl isodecanoate, styrene, and olefins such as ethylene, propylene, butene, pentene, decene, hexadecene, and so on.

G. Finish Enhancers

Preferably, the claimed compositions contain one or more compounds that enhance the finish of the composition after it is applied to skin. Preferred finish enhancers are synthetic elastomers which may be silicone elastomers or organic polymers having elastomeric properties. The term "elastomer" means a compound exhibits properties associated with rubber such as extensibility with applied force, retractibility upon release of the force, and lack of permanent deformation as a result of extension. Rubber like properties are generally seen in high molecular weight cross-linked polymers having weak intermolecular forces. Preferred elastomers are generally in the solid particulate form having particle size ranging from about 0.05 to 75 microns. The claimed compositions preferably comprise about 0.1–25%, preferably about 0.5–15%, more preferably about 1–10% of one or more elastomers. Elastomers provide a velvety smooth finish to the composition, improved spreadability and blendability, and a light, nongreasy feel.

1. Synthetic Organic Polymeric Elastomers

A variety of cross-linked synthetic polymeric elastomers may be used as finish enhancers, including those polymerized from various types of ethylenically unsaturated monomers such as acrylic acid, methacrylic acid, and simple esters thereof, vinyl monomers such as vinyl acetate, vinyl isodecanoate, methyl vinyl ether; maleic anhydride. These monomers may be copolymerized with one or more organic compounds such as esters, glycols, fatty acids, and so on. Examples of such polymers include acrylates/VA crosspolymer, acrylates/vinyl isodecanoate crosspolymer, adipic acid/diethylene glcyol/glycerin crosspolymer, allyl methacrylates crosspolymer, HDI/trimethylolhexyllactone crosspolymer, lauryl acrylate/VA crosspolymer, methyl methacrylate crosspolymer, PVM/MA decadiene crosspolymer, PEG crosspolymer, PPG-35/PPG-51 glyceryl ether/IPDI crosspolymer, trimethyl pentanediol/adipic acid/glycerin crosspolymer, and so on. Particularly preferred is HDI/trimethylolhexyllactone crosspolymer which is a crosslinked condensation polymer formed from the reaction of hexyldiisocyanate with the esterification product of trimethylolpropane with 6 to 7 moles of hexyllactone. This polymer is available from Kobo Products under the tradename BPD-500 which is a combination of silicate and the polymer having the INCI name HDI/trimethylol hexyllactone crosspolymer (and) silica. It is a fine white powder having a particle size of about 5–20 microns comprising about 95–99% polymer and 1–5% silica.

2. Silicone Elastomers

Also suitable for use as finish enhancers are silicone elastomers such as those disclosed in U.S. Pat. No. 6,171,581 which is hereby incorporated by reference in its entirety. Examples of such elastomers include cetearyl dimethicone/vinyl dimethicone crosspolymer, dimethicone copolyol crosspolymer, dimethicone crosspolymer, dimethicone/phenyldimethicone crosspolymer, dimethicone/vinyl dimethicone crosspolymer, and mixtures thereof.

I. Other Ingredients

The claimed composition may contain one more additional ingredients such as fragrances, preservatives, antioxidants, alpha or beta hydroxy acids, or mixtures thereof. A suggested range for the totality of such ingredients is about 0.001 to 3% based on the total weight of the composition. Typical fragrances include parabens and phenoxyethanol. Suitable antioxidants include BHA, BHT, and the like. Suitable alpha or beta hydroxy acids include glycolic, malic, lactic, and salicylic acids.

The invention will be further described in connection with the following Examples, which are set forth for the purpose of illustration only.

EXAMPLE 1

Foundation makeup compositions were prepared as follows:

| | w/w % | | |
|---|---|---|---|
| | 1 | 2 | 3 |
| 1 Cyclomethicone[1] | 20.00 | 19.50 | 22.24 (oil) |
| 1 Titanium dioxide/methicone (ultrafine)[2] | 1.00 | 1.00 | 2.00 (pigment) |
| 1 Titanium dioxide/methicone[2] | 8.00 | 8.00 | 6.00 (pigment) |
| 1 Silica | 1.00 | 1.00 | 1.00 (pigment) |
| 1 Nylon-12 | 2.00 | 2.00 | 2.00 (pigment) |
| 1 Yellow iron oxide/methicone | 0.98 | 0.98 | 1.12 (pigment) |
| 1 Red iron oxide/methicone/boron nitride | 0.62 | 0.62 | 0.98 (pigment) |
| 1 Black iron oxide/methicone | 0.11 | 0.11 | 0.17 (pigment) |
| 1 Zinc oxide/dimethicone | 2.05 | 2.05 | 2.05 (pigment) |
| 1 Boron nitride | 1.69 | 1.69 | 1.51 (pigment) |
| 1 Talc/methicone | 1.60 | 1.60 | 1.72 (pigment) |
| 1 HDI/trimethylol hexyllactone crosspolymer[3] | 2.50 | 2.50 | 2.00 (synthetic elastomer) |
| 2 Cyclomethicone/dimethicone copolyol[4] | 5.00 | 6.00 | 5.50 (oil/surfactant) |
| 2 Phytantriol | 0.10 | 0.10 | 0.10 (skin conditioner) |
| 2 Cyclomethicone/dimethicone[5] | 1.00 | 1.50 | 0.50 (oil) |

| | w/w % | | |
|---|---|---|---|
| | 1 | 2 | 3 |
| 2 Cyclomethicone/trimethylsiloxysilicate[6] | 5.00 | 5.00 | 5.00 (oil/film former) |
| 3 Panthenyl ethyl ether | 0.30 | 0.30 | 0.50 (skin conditioner) |
| 3 Water | 36.99 | 36.99 | 35.20 |
| 3 Panthenol | 0.30 | 0.30 | 0.30 (skin conditioner) |
| 3 Sodium chloride | 0.50 | 0.50 | 0.50 (emulsion stabilizer) |
| 3 Trisodium EDTA | 0.01 | 0.01 | — (preservative) |
| 3 Tetrasodium EDTA | — | — | 0.01 (preservative) |
| 4 Butylene glycol | 2.00 | 2.00 | 2.00 (humectant) |
| 4 Methylparaben | 0.25 | 0.25 | — (preservative) |
| 4 Polyquaternium-51 | — | — | 0.50 (skin conditioner) |
| 5 Ethyl alcohol | 5.00 | 4.00 | — (volatile solvent) |
| 6 Butylene glycol/mushroom extract | 2.00 | 2.00 | 2.00 (skin conditioner/mushroom extract) |
| 7 Phenoxyethanol/parabens | — | — | 1.00 (preservative) |
| 7 Methyldihydrojasmonate | — | — | 0.30 (fragrance) |

[1]Dow Corning 245 fluid, Dow Corning Corporation.
[2]Color Techniques.
[3]Kobo Products Inc.
[4]3225C Formulation Aid, Dow Corning Corporation. A mixture of 90 parts D4/D5 cyclomethicone (decamethylcyclopentasiloxane and decamethylcyclotetrasiloxane) and 10 parts of dimethicone copolyol.
[5]Brooks Industries Gel Base Sil.
[6]Dow Corning 749 Fluid, a mixture of 50 parts trimethylsiloxysilicate and 50 parts of a mixture of volatile silicones comprised of D4/D5 cyclomethicone.

In a main beaker the Sequence 1 ingredients are combined and mixed well until the pigments are fully dispersed. The Sequence 2 ingredients are added to Sequence 1 and mixed well. Meanwhile, the Sequence 3 ingredients are combined in a separate container and mixed well, and the Sequence 4 ingredients are combined in another separate container and mixed well. The Sequence 3 and 4 mixtures are combined with mixing. The Sequence 5 and 6 ingredients are then added to the mixture of Sequence 3 and 4 ingredients and mixed well. Then the beaker container the mixture of Sequences 3, 4, 5, and 6 are combined with the first beaker containing Sequences 1 and 2 and mixed well until emulsified. After emulsification, the Sequence 7 ingredients are added to the composition and mixed well. The composition is poured into glass bottles for storage.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:

1. A method for reducing the shiny appearance of oily skin and/or cosmetically improving the appearance of skin imperfections, comprising applying to the skin an emulsion cosmetic composition comprising a cosmetically effective amount of mushroom extract from the genus Fomes or Polyporus.

2. The method of claim 1 wherein the cosmetic composition is applied to the skin in the form of a foundation makeup.

3. The method of claim 2 wherein the foundation makeup contains one or more skin conditioning agents.

4. The method of claim 1 wherein the skin imperfections are wrinkles, fine lines, or blemishes.

5. The method of claim 1 wherein the emulsion is a water-in-oil emulsion.

6. The method of claim 1 wherein the emulsion is an oil-in-water emulsion.

7. The method of claim 2 wherein the foundation makeup contains one or more metal oxides.

8. The method of claim 7 wherein the metal oxides are oxides of zinc, titanium, iron, or mixtures thereof.

9. The method of claim 8 wherein the wherein the metal oxides are white or colorless.

10. The method of claim 8 wherein the metal oxides are colored.

11. The method of claim 1 wherein the mushroom extract is obtained from *Polyporus officinalis*.

12. The method of claim 1 wherein the mushroom extract has a pH ranging from about 4.8 to 5.2.

13. The method of claim 1 wherein the composition comprises from about 0.01 to 10% by weight of mushroom extract.

14. The method of claim 1 wherein the composition is a skin cream or lotion.

15. The method of claim 1 wherein the composition is an oil in water emulsion foundation makeup composition comprising, by weight of the total composition:
- about 0.01–10% mushroom extract,
- about 1–75% water,
- about 0.1–20% pigment, and
- about 0.5–35% oil.

16. The method of claim 15 wherein the composition further comprises a skin conditioning agent.

17. The method of claim 15 wherein the skin conditioning agent is a quaternary ammonium compound, an alcohol, or mixtures thereof.

18. The method of claim 1 wherein the oil in the emulsion composition is a silicone oil.

* * * * *